United States Patent [19]

Lo et al.

[11] Patent Number: 5,508,011
[45] Date of Patent: Apr. 16, 1996

[54] METHOD AND GENERATION FOR GENERATING 90 Y FROM 90 SR

[75] Inventors: Jiunn-Guang Lo; Jui-Tang Chuang, both of Hsinchu, Taiwan

[73] Assignee: National Tsing Hua University, Hsinchu, Taiwan

[21] Appl. No.: 449,491

[22] Filed: May 24, 1995

[51] Int. Cl.⁶ .................................................. C01F 13/00
[52] U.S. Cl. .................................................. 423/2
[58] Field of Search .................................. 423/2, 1, 155

[56] References Cited

U.S. PATENT DOCUMENTS 5,346,618   9/1994   Horwitz et al. .................... 210/198

Primary Examiner—Donald P. Walsh
Assistant Examiner—Anthony R. Chi
Attorney, Agent, or Firm—Christie, Parker & Hale

[57] ABSTRACT

The present invention is related to a method for generating $^{90}Y$ from $^{90}Sr$ which includes steps of a) providing a crown-ether bonded silica gel, and b) having $^{90}Sr$ stay with the crown-ether silica gel for a period of time. The present invention is also related to a $^{90}Sr/^{90}Y$ generator for implementing the method, which includes a $^{90}Sr/^{90}Y$ converting device including the crown-ether bonded silica gel for adsorbing $^{90}Sr$ and converting $^{90}Sr$ into $^{90}Y$, and an eluting device forcing an eluant to elute the $^{90}Sr/^{90}Y$ converting device to obtain $^{90}Y$. The generator according to the present invention has advantages of simplicity, reusability, high yield and low cost. The obtained $^{90}Y$ by the present method possesses high purity so that it is suitable for nuclear medicine use.

20 Claims, 1 Drawing Sheet

METHOD AND GENERATION FOR GENERATING 90 Y FROM 90 SR

FIELD OF THE INVENTION

The present invention is related to a method for generating career-free $^{90}$Y, and more particularly to a method for generating career-free $^{90}$Y from $^{90}$Sr, and the present invention is also related to a generator for implementing the method.

BACKGROUND OF THE INVENTION $^{90}$Y is a pure β radioactive nuclide which has high energy (Emax=2.28 MeV) and short half-life (T½=64 hours). Owing to the excellent nuclear characters, $^{90}$Y is so far the most popular radioactive nuclide for the therapy and application in nuclear medicine field. However, the half-life of $^{90}$Y is too short to be stored in a product form, so it is more practical for producing $^{90}$Y by a generator which generates $^{90}$Y when it is required.

A conventional method for generating $^{90}$Y from $^{90}$Sr includes steps of converting $^{90}$St into $^{90}$Y and then separating $^{90}$Y from $^{90}$Sr by solvent extraction. Solvent extraction has disadvantages of production of organic wastes and great amount of reagent consumption.

An ion-exchange method can also be used for generating $^{90}$Y from $^{90}$Sr. By this method, $^{90}$Y is obtained through column chromatography which is a simpler process that the solvent extraction method. In the past, several ion-exchange systems have been used in this field, for example, a citrate, lactate, oxalate, acetate or EDTA system. However, the required column for effectively separating $^{90}$Y from $^{90}$Sr is quite long and thus the required amount of the elutant is also large. Accordingly, the cost will be too high. There is also an isotope-exchange method used for generating $^{90}$Y from $^{90}$Sr, but it is unsuitable for being repeatedly used. Of course, some new ion-exchange methods are developed or being developing now.

SUMMARY OF THE INVENTION

An object of the present invention is to provide a method for producing $^{90}$Y from $^{90}$Sr, which can easily separate $^{90}$Y from $^{90}$Sr.

Another object of the present invention is to provide a method for producing $^{90}$Y from $^{90}$Sr, wherein the use of silica gel for serving as an adsorbing matrix is more economical than the use of ion-exchange resin in the conventional methods.

Another object of the present invention is to provide a method for producing $^{90}$Y from $^{90}$Sr, which can obtain a high $^{90}$Y yield.

A further object of the present invention is to provide a generator for generating $^{90}$Y from $^{90}$Sr, which can repeatedly produce high-purity $^{90}$Y.

In accordance with the present invention, a method for generating $^{90}$Y from $^{90}$Sr comprising steps of a) providing a crown-ether bonded silica gel, and b) having $^{90}$Sr stay with the crown-ether silica gel for a period of time.

In accordance with another aspect of the present invention, the crown-ether bonded silica gel is obtained by admixing a clean silica gel with a crown-ether solution, and then evaporating solvent in the crown-ether solution in a rotary evaporator. The clean silica gel is a commercial silica gel preferably treated with heating at 120° C., washing with dimethyl dichlorosilane in a vibrator and then with methanol, and drying.

In accordance with another aspect of the present invention, the period of time in the step b) depends on a conversion rate of $^{90}$Sr into $^{90}$Y.

In accordance with another aspect of the present invention, the present method preferably further includes after the step b) a step c) of eluting the crown-ether bonded silica gel with an organic acid compound. The step c) is executed preferably in a batch mode.

In accordance with another aspect of the present invention, the organic acid compound is picric acid, and the present method preferably includes before the step b) a step of immersing the crown-ether bonded silica gel in picric acid.

In accordance with another aspect of the present invention, a $^{90}$Sr/$^{90}$Y generator for implementing the method includes a $^{90}$Sr/$^{90}$Y converting device including the crown-ether bonded silica gel for adsorbing $^{90}$Sr and convening $^{90}$Sr into $^{90}$Y, and an eluting device forcing an eluant to elute the $^{90}$Sr/$^{90}$Y converting device to obtain $^{90}$Y.

In accordance with another aspect of the present invention, the $^{90}$Sr/$^{90}$Y converting device is a chromatographic column having the crown-ether bonded silica gel as a stationary phase thereof. The eluting device includes an eluant container for loading therein the eluant, and a driving device forcing the eluant to flow through the $^{90}$Sr/$^{90}$Y converting device to have the obtained $^{90}$Y flow out of the $^{90}$Sr/$^{90}$Y converting device with the eluant.

In accordance with another aspect of the present invention, the eluant container can be a residual space of the $^{90}$Sr/$^{90}$Y converting device and the driving device is a gas supplier. Alternatively, the eluant container can be a container communicating with the $^{90}$Sr/$^{90}$Y converting device, and the driving device is a pump or a HPLC.

In accordance with another aspect of the present invention, the $^{90}$Sr/$^{90}$Y generator preferably further includes a collector for collecting the obtained $^{90}$Y.

In accordance with another aspect of the present invention, the eluant can be picric acid.

BRIEF DESCRIPTION OF THE DRAWING

The present invention may best be understood through the following description with reference to the accompanying drawings, in which.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
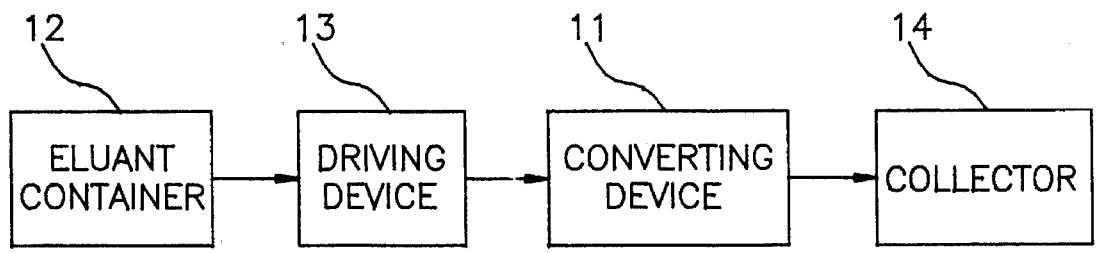
FIG. 1 is a schematic block diagram showing a first preferred embodiment of a $^{90}$Sr/$^{90}$Y generator according to the present invention.

The first preferred embodiment of a $^{90}$Sr/$^{90}$Y generator according to the present invention is described as follows with reference to FIG. 1. In this preferred embodiment, the $^{90}$Sr/$^{90}$Y converting device 11 is a chromatographic column, wherein:

Stationary phase: crown-ether bonded silica gel

A commercial silica gel is cleaned by being treated with heating at 120° C., washing with dimethyl dichlorosilane in a vibrator and then with methanol, and drying before use. The cleaned silica gel is added thereto proper amount of crown-ether, and then dried in a rotatory evaporator to obtain the crown-ether bonded silica gel. The crown-ether bonded silica gel is immersed in picric acid for use.

Mobile phase: 0.01 M picric acid 20 ml 0.01 M picric acid is used in each batch.

Column packing:

Conventional methods can be used for packing the crown-ether bonded silica gel in a glass column which is 20 cm in length and 0.7 cm in ID. The equilibratory solvent is picric acid.

Eluant container 12: beaker or flask

The eluant container 12 is used for loading the eluant, i.e. picric acid.

Driving device 13: HPLC or pump

The driving device 13 is used for forcing the eluant to flow through the $^{90}$Sr/$^{90}$Y converting device 11 to have the obtained $^{90}$Y flow out of the $^{90}$Sr/$^{90}$Y converting device 11 with the eluant. The operation method of the HPLC or pump is well known to those skilled in the art and is not to be redundantly described here.

Collector 14: fraction collector or glass container

The collector 14 is used for collecting the obtained $^{90}$Y.

Preparation for carrier-free $^{90}$Y:

Proper amount of $^{90}$Sr is applied to the $^{90}$Sr/$^{90}$Y converting device 11, i.e. the chromatographic column, and then the eluant, picric acid, is applied to elute the converting device 11 in batch mode. 20 ml eluant is used in each batch and the solution obtained through the converting device 11 contains carrier-free $^{90}$Y. The first 20 ml is preferably discarded. The interval between two elution operations depends on the desired conversion rate of $^{90}$Sr into $^{90}$Y. In other words, the period of time that $^{90}$Sr stays in the converting device 11 with the crown-ether silica gel depends on the conversion rate of $^{90}$Sr into $^{90}$Y. The longer $^{90}$Sr stays in the converting device 11, the greater the conversion rate (see Tables 1 and 2). Table 1 illustrates $^{90}$Y fractions (in %) in total activity of $^{90}$Sr and $^{90}$Y during various periods of staying time. Table 2 illustrates the radioactivity of $^{90}$Y (in mCi) for a 100 mCi $^{90}$Sr during various periods of staying time.

TABLE 1

$^{90}$Y fractions (in %) in total activity of $^{90}$Sr and $^{90}$Y during various periods of staying time (0 hour ~ 10 days and 20 hours).

| a | b | 0 hr | 4 hr | 8 hr | 12 hr | 16 hr | 20 hr |
|---|---|---|---|---|---|---|---|
| 0 day | | 0.000 | 4.057 | 7.645 | 10.838 | 13.696 | 16.266 |
| 1 day | | 18.589 | 20.695 | 22.613 | 24.364 | 25.969 | 27.444 |
| 2 day | | 28.802 | 30.055 | 31.216 | 32.219 | 33.290 | 34.219 |
| 3 day | | 35.086 | 35.894 | 36.650 | 37.357 | 38.202 | 38.641 |
| 4 day | | 39.225 | 39.774 | 40.290 | 40.776 | 41.235 | 41.667 |
| 5 day | | 42.075 | 42.461 | 42.825 | 43.170 | 43.496 | 43.805 |
| 6 day | | 44.098 | 44.376 | 44.639 | 44.889 | 45.126 | 45.351 |
| 7 day | | 45.565 | 45.769 | 45.962 | 46.146 | 46.321 | 46.487 |
| 8 day | | 46.646 | 46.767 | 46.940 | 47.077 | 47.208 | 47.332 |
| 9 day | | 47.451 | 47.564 | 47.672 | 47.774 | 47.872 | 47.966 |
| 10 day | | 48.055 | 48.141 | 48.222 | 48.300 | 48.374 | 48.445 | a + b: staying time

From Table 1, it can be found that the growth rate of $^{90}$Y increases rapidly in the beginning and then the increase rate gradually slows down. For example, after $^{90}$Sr stays in the converting device 11 for 1~2 days, the $^{90}$Y fraction in total activity of $^{90}$Sr and $^{90}$Y is about 20–30%. After four days, the $^{90}$Y fraction in total activity of $^{90}$Sr and $^{90}$Y is almost 40%. After 32 days, the $^{90}$Y fraction in total activity of $^{90}$Sr and $^{90}$Y can be up to 50%.

TABLE 2

Radioactivity of $^{90}$Y (in mCi) for a 100 mCi $^{90}$Sr during various period of staying time (0 hour ~ 10 days and 20 hours).

| a | b | 0 hr | 4 hr | 8 hr | 12 hr | 16 hr | 20 hr |
|---|---|---|---|---|---|---|---|
| 0 day | | 0.000 | 4.228 | 8.278 | 12.155 | 15.896 | 19.426 |
| 1 day | | 22.833 | 26.095 | 29.221 | 32.212 | 35.078 | 37.824 |
| 2 day | | 40.453 | 42.969 | 45.832 | 47.534 | 49.092 | 52.020 |
| 3 day | | 54.050 | 55.992 | 57.853 | 59.635 | 61.818 | 62.975 |
| 4 day | | 64.541 | 66.041 | 67.076 | 68.850 | 70.619 | 71.430 |
| 5 day | | 72.637 | 73.795 | 74.902 | 75.963 | 76.979 | 77.952 |
| 6 day | | 78.884 | 79.778 | 80.633 | 81.452 | 82.236 | 82.986 |
| 7 day | | 83.705 | 84.396 | 85.055 | 85.687 | 86.239 | 86.870 |
| 8 day | | 87.427 | 87.850 | 88.466 | 88.954 | 89.423 | 89.869 |
| 9 day | | 90.299 | 90.709 | 91.102 | 91.475 | 91.835 | 92.182 |
| 10 day | | 92.511 | 92.831 | 93.132 | 93.424 | 93.701 | 93.968 | a + b: staying time

For example, after 100 mCi $^{90}$Sr stays in the converting device 11 for 1 day, 23 mCi $^{90}$Y is obtained. After 2 days, 40 mCi $^{90}$Y is obtained. Users can elute the converting device 11 after the optimal staying time to produce $^{90}$Y.

Figure 2:
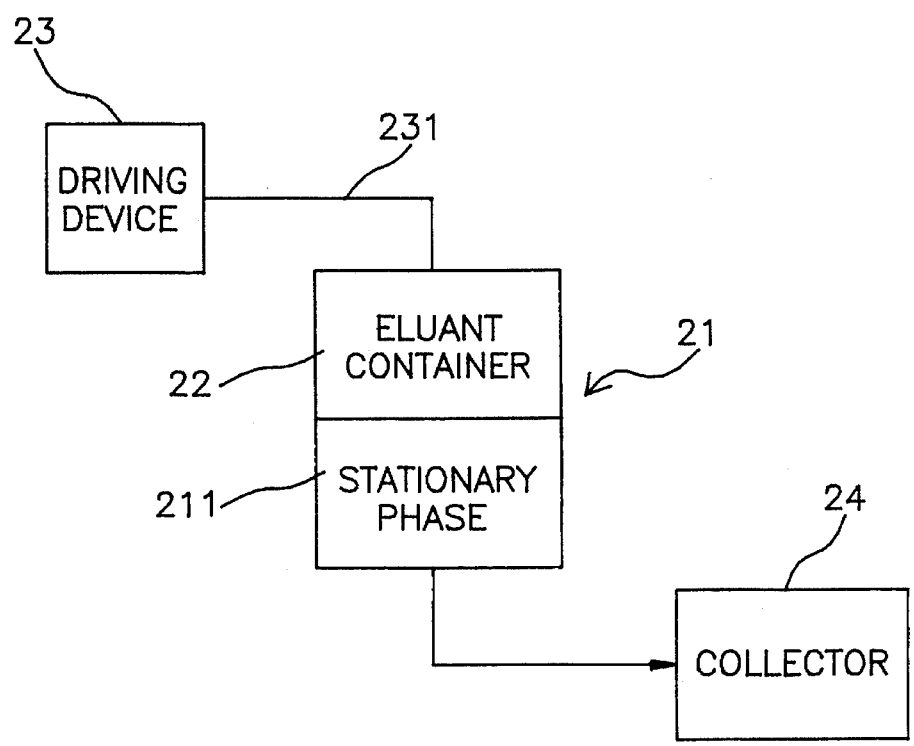
FIG. 2 is a schematic block diagram showing a second preferred embodiment of a $^{90}$Sr/$^{90}$Y generator according to the present invention.

Please refer to FIG. 2 which is a schematic block diagram showing a second preferred embodiment of a $^{90}$Sr/$^{90}$Y generator according to the present invention. The generator includes a $^{90}$Sr/$^{90}$Y converting device 21, an eluant container 22, a driving device 23 and a collector 24. In this preferred embodiment, the $^{90}$Sr/$^{90}$Y convening device 21 is a chromatographic column in which the stationary phase is crown-ether bonded silica gel and the mobile phase is picric acid. The residual space of the $^{90}$Sr/$^{90}$Y converting device serves as the eluant container 22 and the driving device 23 is a gas supplier. The gas supplier applies gas directly to the converting device 21 or through a tube to the convening device 21 to force picric acid to flow through the converting device 21. By this way, $^{90}$Y can also be obtained.

The generator according to the present invention has advantages of simplicity, reusability, high yield and low cost. The obtained $^{90}$Y by the present method possesses high purity so that it is suitable for nuclear medicine use.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for generating $^{90}$Y from $^{90}$Sr, comprising steps of:

a) providing a crown-ether bonded silica gel; and b) having $^{90}$Sr stay with said crown-ether silica gel for a period of time.

2. A method according to claim 1 wherein said crown-ether bonded silica gel is obtained by admixing a clean silica gel with a crown-ether solution, and then evaporating solvent in said crown-ether solution in a rotary evaporator.

3. A method according to claim 2 wherein said clean silica gel is a commercial silica gel treated with heating, washing and drying.

4. A method according to claim 3 wherein said silica gel is heated and dried at 120° C.

5. A method according to claim 3 wherein said silica gel is washed by dimethyl dichlorosilane in a vibrator, and then by methanol.

6. A method according to claim 1 wherein said period of time in said step b) depends on a conversion rate of $^{90}Sr$ into $^{90}Y$.

7. A method according to claim 1 further comprising after said step b) a step c) of eluting said crown-ether bonded silica gel with an organic acid compound.

8. A method according to claim 7 wherein said step c) is executed in a batch mode.

9. A method according to claim 8 wherein said organic acid compound is picric acid.

10. A method according to claim 9 flirther comprising before said step b) a step of immersing said crown-ether bonded silica gel in picric acid.

11. A $^{90}Sr/^{90}Y$ generator for implementing said method as claimed in claim 1, comprising:

a $^{90}Sr/^{90}Y$ converting device including said crown-ether bonded silica gel for adsorbing $^{90}Sr$ and converting $^{90}Sr$ into $^{90}Y$; and an eluting device forcing an eluant to elute said $^{90}Sr/^{90}Y$ convening device to obtain $^{90}Y$.

12. A $^{90}Sr/^{90}Y$ generator according to claim 11 wherein said $^{90}Sr/^{90}Y$ converting device is a chromatographic column having said crown-ether bonded silica gel as a stationary phase thereof.

13. A $^{90}Sr/^{90}Y$ generator according to claim 11 wherein said eluting device includes:

an eluant container for loading therein said eluant; and a driving device forcing said eluant to flow through said $^{90}Sr/^{90}Y$ converting device to have said obtained $^{90}Y$ flow out of said $^{90}Sr/^{90}Y$ converting device with said eluant.

14. A $^{90}Sr/^{90}Y$ generator according to claim 13 wherein said eluant container is a residual space of said $^{90}Sr/^{90}Y$ convening device.

15. A $^{90}Sr/^{90}Y$ generator according to claim 14 wherein said driving device is a gas supplier.

16. A $^{90}Sr/^{90}Y$ generator according to claim 13 wherein said eluant container is a container communicating with said $^{90}Sr/^{90}Y$ converting device.

17. A $^{90}Sr/^{90}Y$ generator according to claim 16 wherein said driving device is a pump.

18. A $^{90}Sr/^{90}Y$ generator according to claim 16 wherein said driving device is a HPLC.

19. A $^{90}Sr/^{90}Y$ generator according to claim 11 further comprising a collector for collecting said obtained $^{90}Y$.

20. A $^{90}Sr/^{90}Y$ generator according to claim 11 wherein said eluant is picric acid.

\* \* \* \* \*